(12) United States Patent
Baraldi

(10) Patent No.: US 6,358,964 B1
(45) Date of Patent: Mar. 19, 2002

(54) ADENOSINE, $A_3$ RECEPTOR MODULATORS

(75) Inventor: Pier G. Baraldi, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 0 days.

(21) Appl. No.: 09/625,583

(22) Filed: Jul. 26, 2000

(51) Int. Cl.[7] .................... C07D 239/70; A61K 31/505

(52) U.S. Cl. ........................ 514/267; 544/251

(58) Field of Search ........................ 544/251; 514/267

(56) References Cited

FOREIGN PATENT DOCUMENTS

WO   WO 97/27177   *  7/1997

OTHER PUBLICATIONS

CAS printout for Francis et al.*

* cited by examiner

Primary Examiner—Richard L. Raymond
Assistant Examiner—Hong Liu
(74) Attorney, Agent, or Firm—Roberts Abokhair & Mardula, LLC

(57) ABSTRACT

The compounds of the formula described herein wherein R, $R^1$, $R^2$ and $R^3$ have the meanings given in the specification, are endowed with $A_3$ adenosine receptor agonist activity. These compounds can be used in a pharmaceutical composition to treat disorders caused by excessive activation of the $A_3$ receptor, or can be used in a diagnostic application to determine the relative binding of other compounds to the $A_3$ receptor. The compounds can be labeled, for example with fluorescent or radiolabels, and the labels used in vivo or in vitro to determine the presence of tumor cells which possess a high concentration of adenosine $A_3$ receptors.

18 Claims, No Drawings

ADENOSINE, $A_3$ RECEPTOR MODULATORS

FIELD OF THE INVENTION

The present invention relates to certain triazoloquinazoline derivatives and their use in the practice of medicine as modulators of adenosine $A_3$ receptors.

BACKGROUND OF THE INVENTION

Three major classes of adenosine receptors, classified as $A^1$, $A_2$, and $A_3$, have been characterized pharmacologically. $A_1$ receptors are coupled to the inhibition of adenylate cyclase through $G_i$ proteins and have also been shown to couple to other second messenger systems, including inhibition or stimulation of phosphoinositol turnover and activation of ion channels. $A_2$ receptors are further divided into two subtypes, $A_{2A}$ and $A_{2B}$, at which adenosine agonists activate adenylate cyclase with high and low affinity, respectively. The $A_3$ receptor sequence was first identified in a rat testes CDNA library, and this sequence, later cloned by homology to other G-protein coupled receptors from a rat brain cDNA library, was shown to correspond to a novel, functional adenosine receptor.

The discovery of the $A_3$ receptor has opened new therapeutic vistas in the purine field. In particular, the $A_3$ receptor mediates processes of inflammation, hypotension, and mast cell degranulation. This receptor apparently also has a role in the central nervous system. The $A_3$ selective agonist IB-MECA induces behavioral depression and upon chronic administration protects against cerebral ischemia. $A_3$ selective agonists at high concentrations were also found to induce apoptosis in HL-60 human leukemia cells. These and other findings have made the $A_3$ receptor a promising therapeutic target. Selective antagonists for the $A_3$ receptor are sought as potential antiinflammatory or possibly antiischemic agents in the brain. Recently, $A_3$ antagonists have been under development as antiasthmatic, antidepressant, antiarrhythmic, renal protective, antiparkinson and cognitive enhancing drugs.

It would be desirable to have additional compounds and methods of preparation and use thereof, which are agonists, partial agonists, and/or antagonists of the adenosine $A_3$ receptor. The present invention provides such compositions and methods.

SUMMARY OF THE INVENTION

Compounds useful as potent modulators of the adenosine $A_3$ receptor, with activity as antagonists of this receptor, and methods of preparation and use thereof, are disclosed.

The compounds have the following general formula:

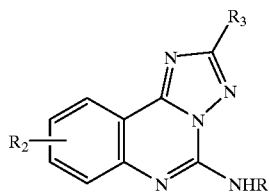

wherein:

R is —C(X)$R_1$, —C(X)—N($R_1$)$_2$, —C(X)O$R_1$, —C(X)S$R_1$, —SO$_n$ $R_1$, —SO$_n$O$R_1$, —SO$_n$S$R_1$, or SO$_n$—N($R_1$)$_2$;

$R_1$ is hydrogen, alkyl, substituted alkyl, alkenyl, substituted alkenyl, alkynyl, substituted alkynyl, aryl, heteroaryl, heterocyclic, lower alkenyl, lower alkanoyl, or, if linked to a nitrogen atom, then taken together with the nitrogen atom, forms an azetidine ring or a 5–6 membered heterocyclic ring containing one or more heteroatoms such as N, O, S;

$R^2$ is hydrogen, halogen, preferably chloro, alkyl, alkenyl, alkynyl, substituted alkyl, substituted alkenyl, substituted alkynyl, aralkyl, substituted aralkyl, heteroaryl, substituted heteroaryl or aryl;

$R^3$ is furan, pyrrole, thiophene, benzofuran, benzypyrrole, benzothiophene, optionally substituted with one or more substituents as described herein for substituted heteroaryl rings;

X is O, S, or N$R^1$;

n is 1 or 2;

radiolabeled analogues thereof, fluorescently labeled analogues thereof, and pharmaceutically acceptable salts thereof, with the proviso that $R^2$ is not halogen when R is —C(X)$R^1$. A preferred R group is —C(X)—N($R^1$)$_2$, where X is O.

Preferably, $R^1$ is hydrogen; $C_{1-8}$ alkyl; $C_{2-7}$ alkenyl, $C_{2-7}$ alkynyl; $C_{3-7}$ cycloalkyl; $C_{1-5}$ alkyl substituted with one or more halogen atoms, hydroxy groups, $C_{1-4}$ alkoxy, $C_{3-7}$ cycloalkyl or groups of formula —N$R^1_2$, —C(O)N$R^1_2$; aryl, substituted aryl wherein the substitution is selected from the group consisting of $C_{1-4}$ alkoxy, $C_{1-4}$ alkyl, nitro, amino, cyano, $C_{1-4}$ haloalkyl, $C_{1-4}$ haloalkoxy, carboxy, carboxyamido; $C_{7-10}$ aralkyl in which the aryl moiety can be substituted with one or more of the substituents indicated above for the aryl group; a group of formula —(CH$_2$)m—Het, wherein Het is a 5–6 membered aromatic or non aromatic heterocyclic ring containing one or more heteroatoms selected from the group consisting of N, O, and S and m is an integer from 1 to 5;

Preferred $C_{1-8}$ alkyl groups are methyl, ethyl, propyl, butyl and isopentyl. Examples of $C_{3-7}$ cycloalkyl groups include cyclopropyl, cyclopentyl, and cyclohexyl. Examples of $C_{1-5}$ alkyl groups substituted with $C_{3-7}$ cycloalkyl groups include cyclohexylmethyl, cyclopentylmethyl, and 2-cyclopentylethyl. Examples of substituted $C_{1-5}$ alkyl groups include 2-hydroxyethyl, 2-methoxyethyl, trifluoromethyl, 2-fluoroethyl, 2-chloroethyl, 3-aminopropyl, 2-(4methyl-1-piperazine)ethyl, 2-(4-morpholinyl)ethyl, 2-aminocarbonylethyl, 2-dimethylaminoethyl, 3-dimethylaminopropyl. Aryl is preferably phenyl, optionally substituted with Cl, F, methoxy, nitro, cyano, methyl, trifluoromethyl, difluoromethoxy groups. Examples of 5 to 6 membered ring heterocyclic groups containing N, O and/or S include piperazinyl, morpholinyl, thiazolyl, pyrazolyl, pyridyl, furyl, thienyl, pyrrolyl, triazolyl, tetrazolyl. Examples of $C_{7-10}$ aralkyl groups comprise benzyl or phenethyl optionally substituted by one or more substituents selected from Cl, F, methoxy, nitro, cyano, methyl, trifluoromethyl, and difluoromethoxy. Preferably, $R^1$ is hydrogen, $C_{1-8}$ alkyl, aryl or $C_{7-10}$ aralkyl, optionally substituted, preferably with halogen atoms. Preferably, X is O, $R_2$ is chloro, $C_{2-3}$ alkyl or substituted alkyl and $R_3$ is furan.

Particularly preferred compounds are those in which R is a phenethyl group in which the phenyl ring is substituted with one or more substituents selected from the group consisting of chlorine, fluorine atoms, methoxy, nitro, cyano, methyl, trifluoromethyl, and difluoromethoxy groups.

The compounds can be used in a method for modulating adenosine $A_3$ receptors in a mammal, including a human.

The methods involve administering an effective amount of a compound of Formula I sufficient to moderate adenosine $A_3$ receptors in the mammal. Uses for the compounds include:

treating hypertension;

treating inflammatory disorders such as rheumatoid arthritis and psoriasis;

treating allergic disorders such as hay fever and allergic rhinitis;

mast cell degranulation;

antitumor agents;

treating cardiac hypoxia; and protection against cerebral ischemia;

diagnostic uses, for example to determine the presence of one or more of the above described medical conditions, or in a screening assay to determine the effectiveness of other compounds for binding to the $A_3$ Ado receptor (i.e., through competitive inhibition as determined by various binding assays), as described in Jacobson and Van Rhee, *Purinergic approaches to experimental therapy*, Jacobson and Jarvis, ed., Wiley, New York, 1997, pp. 101–128; Mathot et al., *Brit. J. Pharmacol.*, 116:1957–1964 (1995); van der Wenden et al., *J. Med. Chem.*, 38:4000–4006 (1995); and van Calenbergh, *J. Med. Chem.*, 40:3765–3772 (1997), the contents of which are hereby incorporated by reference.

The compounds can also be used in a method for fully or partially inhibiting adenylate cyclase ($A_3$) in a mammal, including a human. The methods involve administering an effective amount of a compound of Formula I sufficient to fully or partially inhibit adenylate cyclase in the mammal. The compounds can also be labeled and used to detect the presence of tumor cells containing adenosine $A_3$ ligands in a patient or in a cell sample, by contacting the cells with the labeled compound, allowing the compound to bind to the $A_3$ receptors, and detecting the presence of the label.

The compounds can be used in a pharmaceutical formulation that includes a compound of Formula I and one or more excipients. Various chemical intermediates can be used to prepare the compounds.

DETAILED DESCRIPTION OF THE INVENTION

The present application discloses compounds useful as potent modulators of adenosine receptors, with activity as $A_3$ agonists, and in some cases, $A_3$ antagonists, and methods of preparation and use thereof. The compounds can be used in a method for modulating adenosine $A_3$ receptors in a mammal, including a human. The methods involve administering an effective amount of a compound of Formula I sufficient to moderate adenosine $A_3$ receptors to the mammal.

The compounds can be used in a pharmaceutical formulation that includes a compound of Formula I and one or more excipients. Various chemical intermediates can be used to prepare the compounds.

Definitions

As used herein, a compound is an agonist of an adenosine $A_1$ receptor if it is able to fully inhibit adenylate cyclase ($A_3$) and is able to displace [$^{125}$I]-AB-MECA and/or MRE 3008F20 and its tritiated derivatives in a competitive binding assay.

The formula for a tritiated derivative of MRE 3008F20 is shown below, and its synthesis is described, for example, in Baraldi et al., Bioorg. Med. Chem. Lett., 10:209–210 (2000), the contents of which are hereby incorporated by reference.

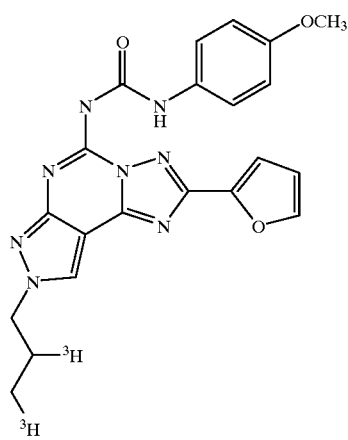

As used herein, a compound is a partial agonist of an adenosine $A_3$ receptor if it is able to partially inhibit adenylate cyclase ($A_3$) and is able to displace [$^{125}$I]-AB-MECA and/or MRE 3008F20 and its tritiated derivatives in a competitive binding assay.

As used herein, a compound is an antagonist of an adenosine $A_3$ receptor if it is able to prevent the inhibition due to an agonist and is able to displace [$^{125}$I]-AB-MECA and/or MRE 3008F20 and its tritiated derivatives in a competitive binding assay.

As used herein, a compound is selective for the $A_3$ receptor if the ratio of $A_1/A_3$ and $A_2/A_3$ activity is greater than about 25, preferably greater than 50, and more preferably, greater than about 100.

As used herein, the term "alkyl" refers to monovalent straight, branched or cyclic alkyl groups preferably having from 1 to 20 carbon atoms, more preferably 1 to 10 carbon atoms ("lower alkyl") and most preferably 1 to 6 carbon atoms. This term is exemplified by groups such as methyl, ethyl, n-propyl, iso-propyl, -butyl, iso-butyl, n-hexyl, and the like. The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc., when modified by "lower," have carbon chains often or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, the term "substituted alkyl" refers to an alkyl group, preferably of from 1 to 10 carbon atoms ("substituted lower alkyl"), having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylarnino, acyloxy, amino, substituted amino aminoacyl, aminoacyloxy, oxyacylamino, cyano, halogen, hydroxyl, keto, thioketo, carboxyl, carboxylalkyl, thiol, thioalkoxy, substituted thioalkoxy, aryl, aryloxy, heteroaryl, heteroaryloxy, heterocyclic, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, aryl, heteroaryl and heterocyclic. As used herein, other moieties having the prefix "substituted" are intended to include one or more of the substituents listed above.

As used herein, "alkaryl" refers to an alkyl group with an aryl substituent. Binding is through the alkyl group. "Aralkyl" refers to an aryl group with an alkyl substituent, where binding is through the aryl group.

As used herein, the term "alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

As used herein, the term "alkynyl" refers to alkynyl groups preferably having from 2 to 10 carbon atoms and more preferably 2 to 6 carbon atoms and having at least 1 and preferably from 1–2 sites of alkynyl unsaturation.

As used herein, the term "acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

As used herein, the term "acylamino" refers to the group —C(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

As used herein, the term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantyl, and the like.

As used herein, the terms "halo" or "halogen" refer to fluoro, chloro, bromo and iodo and preferably is either fluoro or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

"Heterocycle" or "heterocyclic" refers to a monovalent saturated or unsaturated group having a single ring or multiple condensed rings, from 1 to 15 carbon atoms and from 1 to 4 hetero atoms selected from the group consisting of nitrogen, sulfur and oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, of course, that such groups do not contain any substitution or substitution patterns which are sterically impractical and/or synthetically non-feasible.

As used herein, "carboxylic acid derivatives" and sulfonic acid derivatives" refer to —C(X)R$_1$, —C(X)—N(R$_1$)$_2$, —C(X)OR$_1$, —C(X)SR$_1$, —SO$_n$ R$_1$, —SO$_n$OR$_1$, —SO$_n$SR$_1$, or SO$_n$—N(R$_1$)$_2$, where X is O, S or NR$^1$, where R$^1$ is hydrogen, alkyl, substituted alkyl or aryl, and activated derivatives thereof, such as anhydrides, esters, and halides such as chlorides, bromides and iodides, which can be used to couple the carboxylic acid and sulfonic acid derivatives to the 5'-amine using standard coupling chemistry.

"Pharmaceutically acceptable salts" refers to pharmaceutically acceptable salts of a compound of Formula I, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

The following abbreviations are used herein: Abbreviations: [$^{125}$I]AB-MECA, [$^{125}$I]N$^6$-(4-amino-3-iodobenzyl) adenosine-5'N-methyluronamide;(R)-PIA, (R)-N$^6$-(phenylisopropyl)adenosine; DMSO, dimethysulfoxide; I-AB-MECA, N$^6$-(4-amino-3-iodobenzyl)adenosine-5'-N-methyluronamide; IB-MECA, N$^6$-(3-iodobenzyl)adenosine-5'-N-methyluronamide; Ki, equilibrium inhibition constant; NECA, 5'-N-ethylcarboxamido adenosine; THF, tetrahydrofuran; Tris, tris(hydroxymethyl)aminomethane.

Compound Preparation

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amine group converted to an amide or carbamate. Methods of protecting and de-protecting, also known as "blocking" and "de-blocking," are well known and widely practiced in the art, e.g., see T. Green, *Protective Groups in Organic Synthesis*, John Wiley, New York (1981) or *Protective Groups in Organic Chemistry*, Ed. J. F. W. McOmie, Plenum Press, London (1973).

The compounds are preferably prepared by reacting a compound of Formula II below with a suitable carboxylic acid or sulfonic acid derivative using known chemistry.

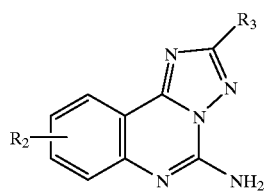

II

Compounds of Formula II can be prepared using the following Schemes I and II, illustrated where R$^3$ is furan.

Scheme I

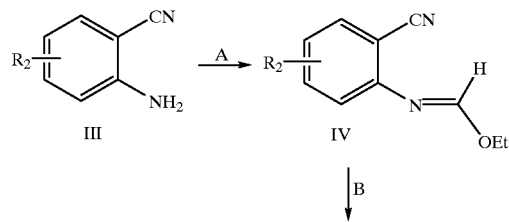

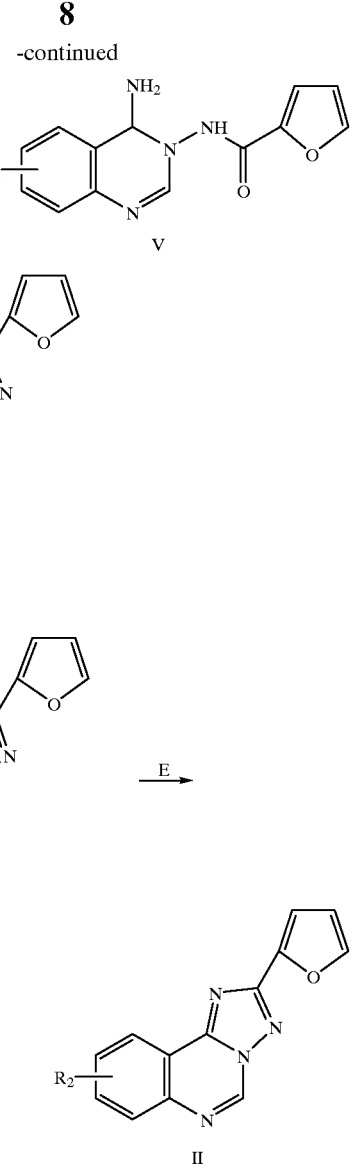

Reagents: A) triethyl orthoformate; B) 2-furoic acid hydrazide, 2-methoxyethanol; C) PhOPh, 260° C.; D) 10% HCl, under reflux; E) cyanamide, pTsOH, N-methylpyrrolidone Scheme II

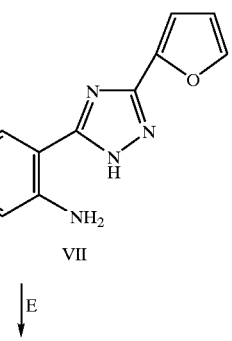

-continued

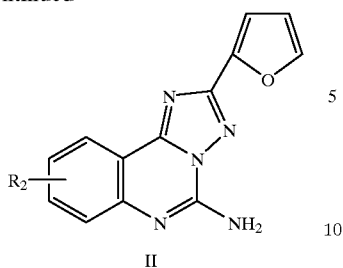

II

Reagents: F) furoic acid hydrazide, diphenyl ether; E) cyanamide, pTsOH, N-methylpyrrolidone.

Scheme II

The compounds of Formula II can be prepared through either an indirect route described in Scheme I or a direct route described in Scheme II. Suitable starting materials for both schemes are the ortho-amino nitrites of Formula III, which can be prepared according to known synthetic procedures.

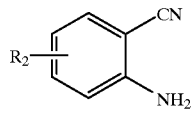

III

Ortho-amino nitrites III are transformed into the corresponding imidates of Formula IV by reaction with an ethyl orthoformate excess at the reflux temperature for 8 to 10 h. The reaction, after evaporation of the ethyl orthoformate, leads to the substantially pure corresponding imidates IV in a high yield as evidenced by the IR and $^1$H NMR analysis on the crude reaction products.

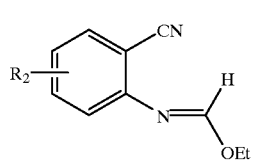

IV

The imidates of Formula IV are then subjected to a sequence of two reactions allowing to obtain the tricyclic structures of Formula VI in a high yield.

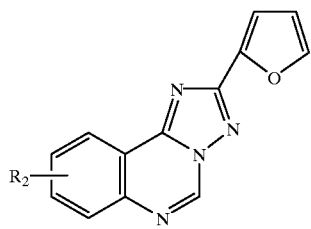

VI

The reaction sequence includes: a) reaction with 2-furoic acid hydrazide in a 2-methoxyethanol solution at the reflux temperature for 8–10 h, to obtain the intermediates compounds of Formula V; b) thermal cyclization of the latter to corresponding compounds of Formula VI, by heating in diphenyl ether at the temperature of 260° C. for 0.5 to 1 h.

The tricyclic compounds VI are then hydrolyzed with HCl at reflux for 1 to 3 h to give triazoles VII, which are finally cyclized to desired compounds II with cyanamide in N-methyl pyrrolidone at reflux and in the presence of para-toluenesulfonic acid (Scheme I).

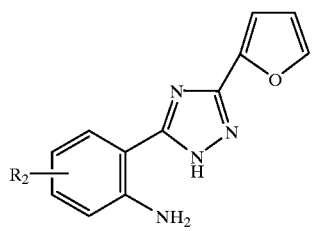

VII

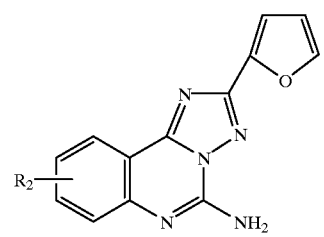

II

In some cases, compounds of Formula VII can be obtained directly heating ortho-amino nitrile III with 2-furoic acid hydrazide in diphenyl ether. The compounds of Formula VII are then cyclized as described above in Scheme II).

Finally, the 5-amine-containing compounds II are reacted with carboxylic acids, sulfonic acids, activated carboxylic acids, activated sulfonic acids, thiocarboxylic acids, activated thiocarboxylic acids, and the like, to form the desired compounds. Activated carboxylic acids include acid halides, esters, anhydrides and other derivatives known to react with amines to form amides, thioamides and the like. Activated sulfonic acids include sulfonyl halides such as sulfonyl chlorides.

It is not necessary in all cases to use activated carboxylic acid and sulfonic acid derivatives. The acids themselves can be coupled to the amines using standard coupling chemistry, for example using dicyclohexyl diimide (DCI) and other routinely used coupling agents. Suitable coupling conditions for forming amide linkages are well known to those of skill in the art of peptide synthesis.

Other methods for forming the 5-amine containing compounds such as CGS 15943 are known in the art, and are described, for example, in Francis, et al., Highly selective adenosine A2 receptor agonists in a series of N-alkylated 2-aminoadenosines. *J.Med.Chem.* 34:2570–2579 (1991), the contents of which are hereby incorporated by reference.

Synthesis of Radiolabeled analogues

The compounds can be labeled with any suitable radiolabel. Examples of suitable radiolabels include $^3$H and $^{14}$C, but any substantially non-toxic radiolabel commonly used in pharmacokinetic studies can be used. Means for incorporating radiolabels onto organic compounds are well known to those of skill in the art.

When the compounds are 5-[[substituted-phenyl)amino]carbonyl]amino-9-substituted-2-(2-furyl)-1,2,4-triazolo[1, 5-c]quinazolines, incorporation of a tritium label is fairly straightforward.

In one embodiment, a suitable starting material is a compound in which a phenyl ring includes a double bond.

The double bond can be reacted with tritium in the presence a suitable catalyst, for example palladium on charcoal or other known hydrogenation catalysts.

Alternatively, the tritium label can be present on the compounds used to react with the amino group to form the amides, ureas or other groups at the 5-position. For example, the isocyanates used to prepare the 5-aminocarbonylamino compounds described herein can include a tritium or other radiolabels, and can therefore be easily incorporated into the final product.

In another embodiment, the radiolabel can be incorporated into the molecule while the ring system is being put together. Iodinated compounds can be prepared, for example by incorporating a radioactive iodine into an aromatic compound used to react with the 5-amine group. Incorporation of iodine into aromatic rings is well known to those of skill in the art. It is straightforward to incorporate an iodine atom into the aromatic compounds used to react with the 5-amine group to prepare the compounds described herein.

Accordingly, using no more than ordinary skill in the art, suitable radiolabeled analogues can readily be prepared.

Synthesis of Fluorescently-labeled analogues

As with the radiolabeled compounds, the synthesis of fluorescently-labeled compounds is relatively straightforward. Preferably, the fluorescent groups are present at the $R_2$- position, although substitution at the $R_3$ position is also feasible. In one embodiment, the fluorescent group(s) include a furan ring which can be attached at the $R_3$ position. Alternatively, other aromatic rings can be used. Fluorescent labels are well known to those of skill in the art, and can readily be attached to the compounds described herein using known chemistry.

Methods of Using the Compounds

The compounds can be used for all indications for which agonists and antagonists of the $A_3$ receptor, including:

treating hypertension;

treating inflammatory disorders such as rheumatoid arthritis and psoriasis;

treating allergic disorders such as hay fever and allergic rhinitis;

mast cell degranulation;

antitumor agents;

treating cardiac hypoxia; and protection against cerebral ischemia;

as described, for example, in Jacobson, TIPS May 1998, pp. 185–191, the contents of which are hereby incorporated by reference.

A preferred use for these compounds is in the detection and/or treatment of cancer. As discussed below, tumor cells have been shown to express the $A_3$ receptor. It is believed that the $A_3$ receptor protects the cells from ischemic damage when they do not receive an adequate blood supply. Several commercially available drugs as well as drugs currently in development are geared toward inhibiting VEGF expression, which cuts off the blood supply to the tumor cells. However, agonism of the adenosine $A_3$ receptors can bring about a protective effect, preventing tumor cell death while the cells are not receiving an adequate blood supply. By administering antagonists of these receptors along with anti-VEGF or other anti-angiogenic compounds, the tumor cells can be cut off from a new blood supply, as well as lose the protection from ischemic injury that agonism of the $A_3$ receptors provides.

The compounds can be administered to a patient via any medically acceptable means. Suitable means of administration include oral, rectal, topical or parenteral (including subcutaneous, intramuscular and intravenous) administration, although oral or parenteral administration are preferred.

The amount of the compound required to be effective as a modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 $\mu$g/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 220 mg per day, and a typical dose would be about 150 mg per day. If discrete multiple doses are indicated, treatment might typically be 50 mg of a compound given 3 times per day.

In another embodiment, the radiolabeled compounds can be administered to a patient for purposes of performing an assay to determine the presence or absence of cancerous tumor cells expressing $A_3$ receptors. The compounds described herein as having a relatively high affinity for the $A_3$ receptor subtype are advantageously administered to a patient, and after the compounds bind to the $A_3$ receptors present in the tumor cells, the location of the compounds can be determined by determining the location of the radiolabeled compounds. Devices for determining the location and density of radiolabeled compounds are well known to those of skill in the art. The use of radiolabeled and/or fluorescently labeled compounds during surgery for removal of cancerous tissue can also be advantageous. Often, surgeons need to ensure complete removal of the cancerous tissue. The radiolabeled or fluorescently labeled compounds can be administered to a patient either before or during the surgery, and will bind to the cancer cells present in the patient. The time of administration will vary, depending, among other factors, on the uptake of the particular compound for the particular tumor cells, and the location of the tumor in the body. The surgeon then has a relatively straightforward assay for determining the presence of residual cancer cells after removing the tumor. The presence of residual tumor cells can be determined by measuring fluorescence or radioactivity at the operative site, using analytical devices well known to those of skill in the art.

Detection of cancer cells in vitro can be performed by administering the compounds to a suspension of cells in cell culture media, allowing the compound to bind the adenosine $A_3$ receptors on the cancer cells, and detecting the label.

Formulations

The compounds described above are preferably administered in formulation including an active compound, i.e., a compound of Formula I, together with an acceptable carrier for the mode of administration. Suitable pharmaceutically acceptable carriers are known to those of skill in the art.

The compositions can optionally include other therapeutically active ingredients such as antivirals, antitumor agents, antibacterials, anti-inflammatories, analgesics, and immunosuppresants. The carrier must be pharmaceutically acceptable in the sense of being compatible with the other ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound of Formula (I) which upon dilution with an appropriate solvent give a solution suitable for parental administration above.

For enteral administration, the compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example glycerol or sorbitol.

The compounds can also be administered locally by topical application of a solution, ointment, cream, gel, lotion or polymeric material (for example a Pluronic™, BASF), which may be prepared by conventional methods known in the art of pharmacy. In addition to the solution, ointment, cream, gel, lotion or polymeric base and the active ingredient, such topical formulations may also contain preservatives, perfumes, and additional active pharmaceutical agents.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into a desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Determination of the Degree of Activity for the Compounds

The activity of the compounds can be readily determined using no more than routine experimentation using any of the following assays.

Rat $A_1$ and $A_{2A}$ Adenosine Receptor Binding Assay

Membrane preparations:

Male Wistar rats (200–250 g) can be decapitated and the whole brain (minus brainstem, striatum and cerebellum) dissected on ice. The brain tissues can be disrupted in a Polytron (setting 5) in 20 vols of 50 mM Tris HCl, pH 7.4. The homogenate can then be centrifuged at 48,000 g for 10 min and the pellet resuspended in Tris-HCL containing 2 IU/ml adenosine deaminase, type VI (Sigma Chemical Company, St. Louis, Mo., USA). After 30 min incubation at 37° C., the membranes can be centrifuged and the pellets stored at −70° C. Striatal tissues can be homogenized with a Polytron in 25 vol of 50 mM Tris HCL buffer containing 10 mM $MgCl_2$ pH 7.4. The homogenate can then be centrifuged at 48,000 g for 10 min at 4° C. and resuspended in Tris HCl buffer containing 2 IU/ml adenosine deaminase. After 30 min incubation at 37° C., membranes can be centrifuged and the pellet stored at −70° C. Although assays on rat receptors can be performed, it may be preferable to use human cloned receptors. Such assays are well known to those of skill in the art.

Radioligand Binding Assays:

Binding of [$^3$H]-DPCPX (1,3-dipropyl-8-cyclopentylxanthine) to rat brain membranes can be performed essentially according to the method previously described by Bruns et al., *Proc. Natl, Acad. Sci.* 77, 5547–5551 1980. Displacement experiments can be performed in 0.25 ml of buffer containing 1 nM [$^3$H]-DPCPX, 100 µl of diluted membranes of rat brain (100 µg of protein/assay) and at least 6–8 different concentrations of examined compounds. Non specific binding can be determined in the presence of 10 µM of CHA ($N^6$cyclohexyladenosine) and this is always $\leq 10\%$ of the total binding. Incubation times are typically 120 min at 25° C.

Binding of tritiated adenosine $A_3$ receptor modulators to rat striatal membranes (100 µg of protein/assay) can be performed according to methods described in Zocchi et al., *J. Pharm. and Exper. Ther.* 276:398–404 (1996). In competition studies, at least 6–8 different concentrations of examined compounds should be used. Non specific binding can be determined in the presence of 50 µM of NECA (5'-(N-ethylcarboxamido)adenosine). Incubation time is typically 60 min at 25° C.

Bound and free radioactivity can be separated by filtering the assay mixture through Whatman GF/B glass-fiber filters using a Brandel cell harvester (Gaithersburg, Md., USA). The incubation mixture can be diluted with 3 ml of ice-cold incubation buffer, rapidly vacuum filtered and the filter can be washed three times with 3 ml of incubation buffer. The filter bound radioactivity can be measured, for example by liquid scintillation spectrometry. The protein concentration can be determined, for example, according to a Bio-Rad method (Bradford, *Anal. Biochem.* 72:248 (1976)) with bovine albumin as reference standard.

Human Cloned $A_3$ Adenosine Receptor Binding Assay

Receptor Binding Assays:

Binding assays can be carried out according to methods described in Salvatore et al., *Proc. Natl. Acad. Sci.* 90:10365–10369 (1993). In saturation studies, an aliquot of membranes (8 mg protein/ml) from HEK-293 cells transfected with the human recombinant $A_3$ adenosine receptor (Research Biochemical International, Natick, Mass., USA) can be incubated with 10–12 different concentrations of [$^{125}$I]AB-MECA ranging from 0.1 to 5 nM. Competition experiments can be carried out in duplicate in a final volume of 100 µl in test tubes containing 0.3 nM [$^{125}$I]AB-MECA, 50 mM Tris HCL buffer, 10 mM $MgCl_2$, pH 7.4 and 20 µl of diluted membranes (12.4 mg protein/ml) and at least 6–8 different concentrations of examined ligands.

Incubation time was 60 min at 37° C., according to the results of previous time-course experiments. Bound and free radioactivity were separated by filtering the assay mixture through Whatman GF/B glass-fiber filters using a Brandel cell harvester. Non-specific binding was defined as binding in the presence of 50 µM R-PIA and was about 30% of total binding. The incubation mixture was diluted with 3 ml of ice-cold incubation buffer, rapidly vacuum filtered and the filter was washed three times with 3 ml of incubation buffer. The filter bound radioactivity was counted in a Beckman gamma 5500B γ counter. The protein concentration can be determined according to a Bio-Rad method (3) with bovine albumin as reference standard.

Data Analysis

Inhibitory binding constant, $K_i$, values can be calculated from those of $IC_{50}$ according to the Cheng & Prusoff equation (Cheng and Prusoff, *Biochem. Pharmacol.* 22:3099–3108 (1973)), $K_i=IC_{50}/(1+[C^*]/K_D^*)$, where $[C^*]$ is the concentration of the radioligand and $K_D^*$ its dissociation constant.

A weighted non linear least-squares curve fitting program LIGAND (Munson and Rodbard, *Anal. Biochem.*, 107:220–239 (1990)) can be used for computer analysis of saturation and inhibition experiments. Data are typically expressed as geometric mean, with 95% or 99% confidence limits in parentheses.

EXAMPLES

The following examples illustrate aspects of this invention but should not be construed as limitations. The symbols and conventions used in these examples are intended to be consistent with those used in the contemporary, international, chemical literature, for example the *Journal of the American Chemical Society* ("*J.Am.Chem.Soc.*") and *Tetrahedron.*

Example 1

Preparation of 5-[[substituted-phenyl)amino] carbonyl]amino-9-substituted-2-(2-furyl)-1,2,4-triazolo[1,5-c]quinazolines General procedures for preparing 5-[[substituted-phenyl) amino]carbonyl]amino-9-substituted-2-(2-furyl)-1,2 Amino compound CGS 15943 (10 mmol) is dissolved in freshly distilled THF (15 mL) and the appropriate isocyanate (13 mmol) is added. The mixture is refluxed under argon for 18 hours. Then the solvent is removed under reduced pressure and the residue purified by flash chromatography (ethyl acetate/light petroleum 4/6 v/v) to afford the desired compounds. The following compounds were synthesized following this procedure:

Compound 1 5-[[4-methoxyphenyl)amino]carbonyl]amino-9-chloro-2-(2-furyl)-1,2,4-triazolo[1,5-c]quinazoline Yield: 88%. Pale yellow solid. IR (KBr): 3250–2975, 1665, 1610, 1515, 1450 cm$^{-1}$; $^1$H NMR (CDCl$_3$) δ: 3.80 (s, 3H); 6.65 (dd, 1H, J=2, J=4); 6.87 (d, 1H, J=8); 6.95 (d, 2H, J=11); 7.27 (d, 2H, J=11), 7.53 (d, 1H, J=4); 7.56 (d, 1H, J =8); 7.70 (d, 1H, J=2); 7.79 (s, 1H); 8.53 (bs, 1H); 11.18 (bs, 1H).

Compound 2 5-[[3-chlorophenyl)amino]carbonyl]amino-9-chloro-2-(2-furyl)-1,2,4-triazolo[1,5-c]quinazoline Yield: 88%. Pale yellow solid. IR (KBr): 3280–2955, 1668, 1615, 1510, 1450 cm$^{-1}$; $^1$H NMR (CDCl$_3$) δ: 6.66 (dd, 1H, J=2, J=4); 6.91–7.39 (m, 4H); 7.65 (s, 1H); 7.78–7.89 (m, 3H); 8.06 (d, 1H, J=2); 8.75 (bs, 1H); 10.98 (bs, 1H).

Example 2

Evaluation of the Biological Activity of the Compounds

The compounds described above in Example 1 were evaluated for their biological activity as follows:

CHO Membranes preparation

The expression of the human $A_2$, $A_{2A}$ and $A_3$ receptors in CHO cells has been previously described (Klotz et al., 1998). The cells were grown adherently and maintained in Dulbecco's modified Eagle's medium with nutrient mixture F12 without nucleosides at 37° C. in 5% $CO_2$/95% air. Cells were split two or three times weekly and then the culture medium was removed for membrane preparations. The cells were washed with phosphate-buffered saline and scraped off flasks in ice cold hypotonic buffer (5 mM Tris HCl, 2mM EDTA, pH 7.4). The cell suspension was homogenized with Polytron and the homogenate was centrifuged for 30 min. at 48,000 g. The membrane pellet was re-suspended in 50 mM Tris HCl buffer at pH 7.4 for $A_1$ adenosine receptors, in 50 mM Tris HCl, 10 mM $MgCl_2$ at pH 7.4 for $A_{2A}$ adenosine receptors, in 50 mM Tris HCl, 10 mM $MgCl_2$, 1 mM EDTA at pH 7.4 for $A_3$ adenosine receptors and were utilized for binding and adenylate cyclase assays.

Human cloned $A_1$, $A_{2A}$, $A_{2B}$ and $A_3$ adenosine receptor binding assay Binding of [$^3$H]-DPCPX to CHO cells transfected with the human recombinant $A_1$ adenosine receptor was performed according to the method previously described by Klotz and coworkers (Klotz, K. N.; Cristalli, G.; Grifantini, M.; Vittori, S.; Lohse, M. J., "Photoaffinity labeling of A1 adenosine receptors," *J. Biol. Chem.*, 260, 14659–14664, 1985).

Displacement experiments were performed for 120 min. at 25° C. in 0.20 mL of buffer containing 1 nM [$^3$H]-DPCPX, 20 μL of diluted membranes (50 μg of protein/assay) and at least 6–8 different concentrations of examined compounds. Non-specific binding was determined in the presence of 10 μM of CHA and this is always 10% of the total binding. Binding of [$^3$H]-SCH58261 to CHO cells transfected with the human recombinant A$_{2A}$ adenosine receptors (50 μg of protein/assay) was performed according to Varani et al. (Varani, K; Cacciari, B.; Baraldi, P. G.; Dionisotti, S.; Ongini, E.; Borea, P. A., "Binding affinity of adenosine receptor agonists and antagonists at human cloned A$_3$ adenosine receptors," *Life Sci.*, 63, 81–87, 1998). In competition studies, at least 6–8 different concentrations of compounds were used and non-specific binding was determined in the presence of 50 μM NECA for an incubation time of 60 min. at 25° C.

Binding of [$^3$H]-DPCPX to HEK-293 cells (Receptor Biology, Inc., Beltsville, Md.) transfected with the human recombinant A$_{2B}$ adenosine receptors were performed essentially to the method described by Varani and coworkers (Mol. Pharmacol.). In particular, assays were carried out for 60 min. at 25° C. in 0.1 mL of 50 mM Tris HCl Buffer, 10 mM MgCl$_2$, 1 mM EDTA, 0.1 mM benzamidine pH 7.4, 2 IU/ml adenosine deaminase containing 40 nM [$^3$H]-DPCPX, diluted membranes (20 μg of protein/assay) and at least 6–8 different concentration of tested compounds. Non-specific binding was determined in the presence of 100 μM of NECA and was always 30% of the total binding.

Binding of [$^3$H] MRE3008-F20 to CHO cells transfected with the human recombinant A$_3$ adenosine receptors was performed according to Varani et al. (Mol. Pharmacol.). Competition experiments were carried out in duplicate in a final volume of 250 μL in test tubes containing 1 nM [$^3$H] MRE3008-F20, 50 mM Tris HCl buffer, 10 mM MgCl$_2$, pH 7.4 and 100 μL of diluted membranes (50 μg of protein/assay) and at least 6–8 different concentrations of examined ligands. Incubation time was 120 min. at 4° C., according to the results of previous time-course experiments (Mol. Pharmacol.). Non-specific bindings was defined as binding in the presence of 1 μM of MRE3008-F20 and was about 25% of total binding. Bound and free radioactivity were separated by filtering the assay mixture through Whatman GF/B glass-fiber filters using a Micro-mate 196 cell harvester (Packard Instrument Company). The filter bound radioactivity was counted on Top Count (efficiency 57%) with Micro-Scint 20. The protein concentration was determined according to a BioRad method (Bradford, M. M., "A rapid and sensitive method for the quantification of microgram quantities of protein utilizing the principle of protein dye-binding," *Anal. Biochem.* 72, 248, 1976) with bovine albumin as reference standard.

Adenylate cyclase assay

Membrane preparation was suspended in 0.5 mL of incubation mixture (50 mM Tris HCl, MgCl$_2$ 10 mM, EDTA, 1 mM, pH 7.4) containing GTP 5 μM, 0.5 mM 4-(3-buthoxy-4-methoxybenzyl)-2-imidazolidinone (Ro 20-1274) as phosphodiesterase inhibitor, 2.0 IU/mL adenosine deaminase and pre-incubated for 10 min. in a shaking bath at 37° C. The IB-MECA or antagonists examined plus ATP (1 mM) and forskolin 10 μM were added to the mixture and the incubation continued for a further 10 min. The potencies of antagonists were determined by antagonism of the IB-MECA (100 nM)-induced inhibition of cyclic AMP production. The reaction was terminated by transferring to a boiling water bath. Boiling was for 2 min., and then the tubes were cooled to room temperature and centrifuged at 2,000 g for 10 min. at 4° C. Supernatants (100 μL) were used in competition protein binding assay carried out essentially according to Varani et al. (Mol. Pharmacol. 2000).

Samples of cyclic AMP standards (0–10 pmol) were added to each test tube containing the incubation buffer (trizma base 0.1 M; aminophylline 8.0 mM; 2-mercaptoethanol 6.0 mM, pH 7.4) and [$^3$H]-cyclic AMP in a total volume of 0.5 mL. The binding protein, previously prepared from beef adrenals, was added to the samples previously incubated at 4° C. for 150 min. and, after the addition of charcoal were centrifuged at 2,000 g for 10 min. The clear supernatant (0.2 mL) was mixed with 4 mL of atomlight in a LS-1800 Beckman scintillation counter.

Results and Discussion

Compounds 1 and 2 were tested in radio ligand binding assays for affinity at rat brain A$_1$, A$_{2A}$, A$_{2B}$ and human A$_3$ receptors. Compound 1 bound to human A$_3$ receptors with a binding affinity of 0.14 nM, and compound 2 bound to human A$_3$ receptors (hA$_3$) with a binding affinity of 0.19 nM. Compound 1 showed selectivities of hA$_1$/hA$_3$=43, hA$_{2a}$/hA$_3$=50 and hA$_{2b}$/hA$_3$=158.

The data demonstrate that the quinazoline derivatives described herein bind to human A$_3$ receptors with extremely high affinity.

Example 3

Pharmaceutical Formulations (A) Transdermal System—for 1000 patches

| Ingredients | Amount |
| --- | --- |
| Active compound | 100 g |
| Silicone fluid | 450 g |
| Colloidal silicon dioxide | 2 g |

(B) Oral Tablet—For 1000 Tablets

| Ingredients | Amount |
| --- | --- |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

(c) Injection—for 1000, 1 mL Ampules

| Ingredients | Amount |
| --- | --- |
| Active compound | 10 g |
| Buffering Agents | q.s. |
| Propylene glycol | 400 mg |
| Water for injection | q.s. 1,000 mL |

The active compound and buffering agents are dissolved in the propylene glycol at about 50° C. The water for injection is then added with stirring and the resulting solution is filtered, filled into ampules, sealed and sterilized by autoclaving.

(D) Continuous Injection—for 1000 mL

| Ingredients | Amount |
|---|---|
| Active compound | 10 g |
| Buffering Agents | q.s. |
| Water for injection | q.s. 1000 mL |

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of the following formula:

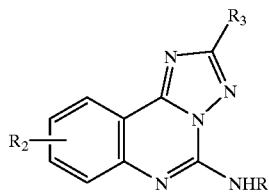

wherein:

R is —C(X)R$_1$, —C(X)—N(R$_1$)$_2$, —C(X)OR$_1$, —C(X)SR$_1$, —SO$_n$R$_1$, —SO$_n$OR$_1$, —SO$_n$SR$_1$, or SO$_n$—N(R$_1$)$_2$;

R$_1$ is hydrogen, alkyl, substituted alkyl, alkenyl, substituted alkenyl, alkynyl, substituted alkynyl, aryl, heteroaryl, heterocyclic, lower alkenyl, lower alkanoyl, or, if linked to a nitrogen atom, then taken together with the nitrogen atom, forms an azetidine ring or a 5–6 membered heterocyclic ring containing one or more heteroatoms such as N, O, S;

R$^2$ is hydrogen, halogen, alkyl, substituted alkyl, aralkyl, substituted aralkyl, heteroaryl, substituted heteroaryl or aryl;

R$^3$ is furan, pyrrole, thiophene, benzofuran, benzypyrrole, benzothiophene, optionally substituted with one or more substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$^2$-aryl, —SO$_2$-heteroaryl, and trihalomethyl;

X is O, S, or NR$^1$;

n is 1 or 2; and and pharmaceutically acceptable salts thereof, with the proviso that R$^2$ is not halogen when R is —C(X)R$^1$.

2. The compound of claim 1 wherein R is selected from the group consisting of ureas, thioureas and sulfonamides.

3. The compound of claim 1, wherein R is —C(X)NHR$_1$ and X is O.

4. The compound of claim 1 wherein R$_1$ is selected from the group consisting of alkyl, alkenyl and aryl.

5. The compound of claim 1 wherein R$_2$ is selected from the group consisting of hydrogen, halogen, alkyl, alkenyl and aryl.

6. The compound of claim 1 wherein R$_3$ is furan.

7. The compound of claim 1 wherein X is O.

8. A method of treating hypertension, inflammation, allergic reaction, mast cell degranulation, cardiac hypoxia, and protecting against cerebral ischemia, comprising administering to a patient in need of treatment thereof an effective amount of a compound of claim 1.

9. The method of claim 8 wherein R is selected from the group consisting of ureas, thioureas and sulfonamides.

10. The method of claim 8 wherein R$^1$ is selected from the group consisting of alkyl, alkenyl and aryl.

11. The method of claim 8 wherein R$_2$ is selected from the group consisting of hydrogen, halogen, alkyl, alkenyl and aryl.

12. The method of claim 8 wherein X is O.

13. The method of claim 8 wherein the disorder to be treated is selected from the group consisting of cardiac hypoxia and cerebral ischemia.

14. A method of treating tumors containing a concentration of adenosine A3 receptors more than the concentration of adenosine A3 receptors in surrounding, normal tissue, comprising administering to a patient in need of treatment thereof an effective amount of a compound of claim 1.

15. The method of claim 14 wherein R is selected from the group consisting of ureas, thioureas and sulfonamides.

16. The method of claim 14 wherein R$_1$ is selected from the group consisting of alkyl, alkenyl and aryl.

17. The method of claim 14 wherein R$_2$ is selected from the group consisting of hydrogen, halogen, alkyl, alkenyl and aryl.

18. The method of claim 14 wherein X is O.

* * * * *